(12) United States Patent
Zeng

(10) Patent No.: US 8,759,369 B2
(45) Date of Patent: Jun. 24, 2014

(54) INHALABLE SOLID AMORPHOUS PARTICLES COMPRISING TIOTROPIUM BROMIDE AND A CO-SOLID

(75) Inventor: Xian-Ming Zeng, Sunny Isles, FL (US)

(73) Assignee: Norton Healthcare Ltd., London (GB)

( * ) Notice: Subject to any disclaimer, the term of this patent is extended or adjusted under 35 U.S.C. 154(b) by 712 days.

(21) Appl. No.: 12/668,546

(22) PCT Filed: Jul. 3, 2008

(86) PCT No.: PCT/GB2008/002294
§ 371 (c)(1),
(2), (4) Date: Apr. 15, 2010

(87) PCT Pub. No.: WO2009/007687
PCT Pub. Date: Jan. 15, 2009

(65) Prior Publication Data
US 2010/0326437 A1    Dec. 30, 2010

Related U.S. Application Data

(60) Provisional application No. 60/958,823, filed on Jul. 9, 2007.

(30) Foreign Application Priority Data

Aug. 16, 2007  (GB) .................................. 0716026.0

(51) Int. Cl.
| | | |
|---|---|---|
| *A61K 31/46* | (2006.01) | |
| *A61K 9/16* | (2006.01) | |
| *A61K 9/19* | (2006.01) | |
| *A61K 9/48* | (2006.01) | |
| *A61M 15/00* | (2006.01) | |
| *A61P 11/06* | (2006.01) | |
| *A61P 11/08* | (2006.01) | |

(52) U.S. Cl.
USPC ............. 514/291; 424/489; 424/451; 424/46; 424/499; 128/203.15

(58) Field of Classification Search
None
See application file for complete search history.

(56) References Cited

U.S. PATENT DOCUMENTS

| | | | |
|---|---|---|---|
| 5,610,163 A | 3/1997 | Banholzer et al. | |
| 6,589,560 B2* | 7/2003 | Foster et al. | 424/489 |
| 6,645,466 B1 | 11/2003 | Keller et al. | |
| 2002/0169321 A1 | 11/2002 | Banholzer et al. | |
| 2003/0070679 A1* | 4/2003 | Hochrainer et al. | 128/203.15 |
| 2003/0087927 A1 | 5/2003 | Sieger et al. | |
| 2003/0171586 A1 | 9/2003 | Banholzer et al. | |
| 2004/0002510 A1 | 1/2004 | Bender et al. | |
| 2005/0121027 A1 | 6/2005 | Nilsson et al. | |
| 2005/0143410 A1 | 6/2005 | Pfrengle et al. | |
| 2006/0246009 A1 | 11/2006 | Morissette et al. | |
| 2007/0092453 A1 | 4/2007 | Pop et al. | |
| 2007/0225314 A1 | 9/2007 | Diulgheroff et al. | |

FOREIGN PATENT DOCUMENTS

| | | |
|---|---|---|
| CA | 2395653 | 4/2002 |
| EP | 0 372 777 | 6/1990 |
| EP | 0 418 716 | 3/1991 |
| EP | 0 616 525 | 9/1994 |
| EP | 1238661 A1 | 9/2002 |
| EP | 1 401 445 | 3/2004 |
| EP | 1 468 998 | 10/2004 |
| EP | 1 487 832 | 12/2004 |
| EP | 1 508 330 | 2/2005 |
| EP | 1 682 542 | 7/2006 |
| EP | 1 923 393 | 5/2008 |
| WO | WO 93/11743 | 6/1993 |
| WO | WO 98/05302 | 2/1998 |
| WO | WO 00/28979 | 5/2000 |
| WO | WO 02/30928 | 4/2002 |
| WO | WO 2004/017942 | 3/2004 |
| WO | WO 2005020953 A1 * | 3/2005 |
| WO | WO 2005027875 A1 * | 3/2005 |
| WO | WO 2006/134021 | 12/2006 |
| WO | WO 2007/075858 | 7/2007 |

OTHER PUBLICATIONS

"PVP", ISP Corp, accessed at http://online1.ispcorp.com/Brochures/Performance%20Chemicals/PVP.pdf, Oct. 2, 2012.*
Brusasco et al., Thorax, 58: 399-404 (2003).*
J.P. Mitchell and M.W. Nagel "Particle Size Analysis of Aerosols from Medicinal Inhalers" KONA No. 22 (2004) 32.
Malcolmson R. J. et al. "Dry Powder Formulations for Pulmonary Delivery" Pharmaceutical Science and Technology Today, Elsevier Trends Journals, Cambridge, GB, vol. 1, No. 9, Dec. 1, 1998, pp. 394-398.
International Search Report, Jun. 4, 2009.

* cited by examiner

*Primary Examiner* — Kortney L Klinkel
*Assistant Examiner* — Lisbeth C Robinson
(74) *Attorney, Agent, or Firm* — RatnerPrestia

(57) ABSTRACT

An inhalable medicament is provided, in particular a new solid-state form of tiotropium bromide. The medicament can be in the form of solid amorphous particles containing an intimate admixture of tiotropium bromide together with a pharmaceutically acceptable co-solid having a glass transition temperature of at least −50° C., such as a sugar and/or sugar alcohol.

21 Claims, No Drawings

INHALABLE SOLID AMORPHOUS PARTICLES COMPRISING TIOTROPIUM BROMIDE AND A CO-SOLID

CROSS-REFERENCE TO RELATED APPLICATIONS

This application is a national phase filing of International Application No. PCT/GB2008/002294, filed Jul. 3, 2008, which claims priority to U.S. Provisional Application No. 60/958,823, filed Jul. 9, 2007, and British Application No. 0716026.0, filed Aug. 16, 2007. The disclosures of International Application No. PCT/GB2008/002294, U.S. Provisional Application No. 60/958,823, and British Application No. 0716026.0 are each incorporated herein by reference in their entirety for all purposes.

FIELD OF THE INVENTION

This invention relates to an inhalable medicament and in particular to a new solid-state form of tiotropium bromide.

BACKGROUND OF THE INVENTION

Tiotropium bromide has the systematic name $(1\alpha,2\beta,4\beta,7\beta)$-7-[(hydroxidi-2-thienylacetyl)oxy]-9,9-dimethyl-3-oxa-9-azoniatricyclo[3.3.1.0$^{2,4}$]nonane and has the following formula:

Tiotropium bromide is known per se and is described in more detail in EP 0 418 716.

Tiotropium bromide is a known muscarinic receptor antagonist and, on topical application, acts predominantly on the $M_3$ muscarinic receptors located in the airways to produce smooth muscle relaxation, thus producing a bronchodilatory effect. Tiotropium bromide is therefore suitable for the treatment of chronic obstructive pulmonary disease (COPD) and asthma.

Several attempts have been made to formulate stable, easy-to-handle solid-state forms of tiotropium bromide for use as an inhalable medicament, to varying degrees of success. EP 1 468 998 discloses crystalline tiotropium bromide monohydrate. EP 1 401 445 and EP 1 682 542 disclose an anhydrous form of crystalline tiotropium bromide. EP 1 487 832 discloses crystalline tiotropium bromide micronisate. US 2005/0676760 discloses crystalline forms of tiotropium bromide selected from an anhydrate, methanol solvate, THF solvate, 1,4-dioxane solvate, dimethylformamide solvate, mixed methylene chloride/methyl ethyl ketone solvate, and 1-butanol solvate. Similarly US 2005/0676807 discloses crystalline forms of tiotropium bromide selected from an anhydrate, 1,4 dioxane solvate, ethanol solvate, methanol solvate, anisol solvate, n-butanol solvate, N,N-dimethyl acetamide solvate, N,N-dimethyl formamide solvate, isopropanol solvate, 1,2-propanediol solvate, pyridine solvate, tert-butanol solvate, terahydrofuran solvate and tetrahydropyran solvate.

SUMMARY OF THE INVENTION

However, there remains a need in the art for solid state forms which are both stable, in particular to moisture, and easy to handle.

Accordingly, the present invention provides solid amorphous particles comprising an intimate admixture of tiotropium bromide together with a pharmaceutically acceptable co-solid having a glass transition temperature of at least −50° C.

DETAILED DESCRIPTION OF THE INVENTION

The present invention therefore provides a new solid-state form of tiotropium bromide. The particles are an intimate admixture of tiotropium bromide and a co-solid defined by its glass transition temperature, such as a sugar, a sugar derivative or a combination thereof. That is, substantially all of the individual particles are composed of both the tiotropium bromide and the co-solid. Preferably the particles consist essentially of tiotropium bromide and the co-solid. Reference is made to substantially all of the particles because it is possible from a purely statistical stand point that a small number of the particles might contain only the co-solid if such particles solidify in the absence of tiotropium bromide.

The particles of tiotropium bromide of the present invention are an amorphous solid, i.e. a glass. That is, the particles are a solid in which there is no long-range order in the positions of the molecules. The amorphous solid is obtained by rapidly cooling an aqueous solution of the components of the solid so that a solid is formed before the molecules can crystallise into a more thermodynamically favourable crystalline state.

The solid particles of the present invention are stable and tend not to absorb water even under conditions of high humidity. This is an important property for an inhalable medicament, particularly when formulated as a dry powder. In addition, the co-solid provides additional bulk to the active ingredient. Tiotropium bromide is highly potent and is typically used in a dose of 18 μg based on the amount of tiotropium. Such small quantities of active ingredient can be difficult to handle and can hinder accurate metering. However, incorporation of the co-solid allows for easier handling and more accurate metering of the active ingredient.

The co-solid used in the particles must be pharmaceutically acceptable which has its standard meaning in the art, namely that it may be incorporated into a medicament. That is, the co-solid will be non-toxic, biodegradable and biocompatible. It will ideally be physicochemically stable and non-hygroscopic.

The co-solid must also have a glass transition temperature of at least −50° C., more preferably at least −25° C. and most preferably at least 0° C. This lower limit on the glass transition temperature ensures that the amorphous (i.e. glass) state is stable at ambient temperature (i.e. 20° C.), and preferably at elevated temperatures that the medicament may experience during storage, e.g. 50° C. or above and even 75° C. or above. By stable is meant that the amorphous state does not crystallise or otherwise degrade. The upper limit to the glass transition temperature is less relevant and is only limited by the practicalities of the lyophilisation process and the co-solids available.

The co-solid is preferably water soluble and more preferably has a water solubility of at least 20 mg per 100 mL at 20° C., more preferably at least 50 mg per 100 mL at 20° C. and most preferably 80 mg per 100 mL.

The co-solid used in the particles of the present invention is typically a sugar or a sugar derivative, or a combination thereof. The derivative may be a sugar polyol or an amino sugar. Sugars, sugar alcohols and amino sugars are well known in the art and the present invention is not restricted to any particular sugar, sugar alcohol or amino sugar. Any sugar, sugar alcohol or amino sugar which is capable of forming an amorphous solid in the presence of tiotropium bromide may be used. Preferably the sugar is a mono or disaccharide, or the derivative is based on a mono or disaccharide. The sugar alcohol is a sugar in which at least one of the carboxyl groups (aldehyde or ketone) in the sugar has been reduced to an alcohol (primary or secondary alcohol). Sugar polyols are sometimes referred to in the art simply as sugar alcohols. The amino sugar is a sugar in which at least one of the hydroxyl groups has been replaced with an amino group. Specific examples of sugars used in the present invention are dextrose, fructose, glucose, lactose, mannose, sucrose and trehalose. Particularly preferred sugars are glucose, lactose, mannose, sucrose and trehalose. Specific examples of sugars alcohols used in the present invention are mannitol, maltitol, sorbitol and xylitol. A particularly preferred sugar alcohol is mannitol. A particularly preferred amino sugar alcohol is glucosamine.

Other examples of suitable co-solids include PEG, HMPC and PLG.

The solid amorphous particles of the present invention may be prepared by lyophilising (freeze drying) an aqueous solution of tiotropium bromide and the sugar and/or sugar derivative. Accordingly, the present invention provides a process for preparing solid amorphous particles of tiotropium bromide comprising lyophilising an aqueous solution of tiotropium bromide together with a sugar and/or a sugar alcohol. Preferably the aqueous solution is prepared by forming an aqueous solution of the sugar and/or sugar derivative, dissolving the tiotropium bromide therein and optionally adjusting the pH to a value from 4 to 6. The process may further comprise micronising the particles.

The aqueous solution may be prepared simply by dissolving the components in water or a mixture of water and a water-miscible pharmaceutically acceptable co-solvent. A suitable co-solvent is an alcohol and preferably methanol, ethanol, n-propanol, iso-propanol, n-butanol, tert-butanol iso-butanol or combinations thereof. In a preferred embodiment, the co-solid, e.g. sugar and/or sugar derivative, is added to an aqueous solvent and the solution is optionally heated to dissolve the co-solid. Once dissolved, the aqueous solution is allowed to cool to provide a hyper-saturated solution. Tiotropium bromide is then added thereto. The mixture may be heated and/or sonicated to dissolve the tiotropium bromide. The resulting solution may be filtered if required and the pH may be adjusted. The preferred pH is from 4 to 6.

The solution is then lyophilised using standard techniques in the art. There are typically three stages in the lyophilisation process, namely freezing, primary drying, and secondary drying.

The freezing step may be performed in a shell freezer by placing the aqueous solution in a freeze-drying flask and rotating the flask in a bath cooled, for example, by mechanical refrigeration, dry ice, methanol or liquid nitrogen. Alternatively, the freezing step may be performed using a freeze-drying machine. In the freeze drying machine, fine droplets of the aqueous solution are sprayed into the refrigerant, e.g. liquid nitrogen. The freeze drying machine is preferred for the industrial preparation of the material.

During the primary drying step the pressure is lowered and enough heat is supplied to the material for the aqueous solution to sublimate. The secondary drying step may be used if required to sublimate the solvent molecules that are adsorbed during the freezing step.

The mean particle diameter of the solid amorphous particles of the present invention is preferably 1-10 microns and more preferably 1-5 microns. The particles size of the particles disclosed herein is the aerodynamic particle size. See J. P. Mitchell and M. W. Nagel in "Particle size analysis of aerosols from medicinal inhalers" KONA No. 22 (2004) 32 for further details concerning the measurement of particles sizes. The appropriate particle size may be provided by the lyophilisation process described hereinabove although further micronisation may be performed by grinding in a mill, e.g. an air jet, ball or vibrator mill, by sieving, by crystallization, by spray-drying or by further lyophilisation.

The present invention further provides solid amorphous particles obtainable by the above-described process. The particles thus formed are characterised by the intimate admixture of the tiotropium bromide and the co-solid, e.g. the sugar and/or sugar derivative.

The weight ratio of tiotropium bromide to sugar and/or a sugar alcohol in the particles is from 1:1 to 1:1000, preferably from 1:10 to 1:500 (measured as a property of the bulk material).

The present invention also provides an inhalable medicament comprising the particles described herein and one or more pharmaceutically acceptable excipients. The pharmaceutically acceptable excipients include carriers, including diluents, propellants, surfactants, and flavourings (see Remington's Pharmaceutical Sciences, 18th Ed., Gennaro, Mack Publishing Co., Easton, Pa. 1990 and Remington: The Science and Practice of Pharmacy, Lippincott, Williams & Wilkins, 1995). The pharmaceutical composition may be a dry powder for a dry-powder inhaler in which the one or more pharmaceutically acceptable excipients includes an inert carrier, or an aerosol for a pressurised metered-dose inhaler in which the one or more pharmaceutically acceptable excipients includes a propellant.

Examples of particulate carriers for preparing an inhalable dry powder include lactose, glucose, or sodium starch glycolate, preferably lactose and most preferably alpha lactose monohydrate. In general, the particle size of the carrier should be such that it can be entrained in an air stream but not deposited in the key target sites of the lung. Accordingly, the carrier preferably has a mean particle size of 40 microns or more, more preferably the carrier particles have a VMD of 50-250 microns. The particle size may be determined using laser light scattering (Sympatec GmbH, Claasthal-Zellerfeld, Germany).

The dry powder composition may be metered and filled into capsules, e.g. gelatin or hydroxypropyl methylcellulose capsules, such that the capsule contains a unit dose of active ingredient When the dry powder is in a capsule containing a unit dose of active ingredient, the total amount of composition will depend on the size of the capsules and the characteristics of the inhalation device with which the capsules are being used. However, typical examples of total fill weights of dry powder per capsule are 1-25 mg. Alternatively, the dry powder composition according to the invention may be filled into the reservoir of a multi-dose dry powder inhaler (MDPI), for example of the type disclosed in WO 92/10229. Such inhalers comprise a chassis, a dosing chamber, a mouthpiece and the medicament The particles of the present invention may also be formulated as an aerosol. Examples of a propellant gas for preparing an aerosol formulation include HFA134a, HFA227 or mixtures thereof. See EP 0 372 777, EP 0 616 525 and WO 98/05302 for further details of aerosol formulations. Pressured metered-dose inhalers of this type typically comprise a chassis, a mouthpiece and a canister comprising the medicament as described in the aforementioned documents.

The present invention will now be described with reference to the following examples which are not intended to be limiting.

EXAMPLES

Example 1

Lactose is added to water and the solution is heated to dissolve the lactose. Once dissolved, the aqueous solution is allowed to cool to provide a hyper-saturated solution. Tiotropium bromide is added such that the ratio of lactose to tiotropium bromide is 100 parts by weight lactose to one part by weight tiotropium bromide. The mixture is sonicated to dissolve the tiotropium bromide. The resulting solution is then filtered through filter paper and the pH is adjusted to 5.

The solution is then transferred to a round-bottomed flask and the flask is submerged in liquid nitrogen. The flask is swirled such the inside wall of the flask becomes coated in a thin layer of a solid material. The flask is then placed under vacuum at a temperature of −20° C. for 24 hours to produce fluffy particles. The particles are collected and micronised so that they are suitable for inhalation.

Example 2

An aqueous solution of tiotropium bromide and lactose is formed as set out in Example 1. The solution is placed into a freeze-drier which sprays small droplets (about 10 μm) into liquid nitrogen. The particles are collected and placed in a vacuum freezer for 24 hours. The resulting particles are suitable for inhalation and do not require micronisation. The particles may, however, be micronised if desired.

Example 3

An inhalable medicament is formed by combining the particles formed in Examples 1 or 2 with coarse lactose using techniques described in, for example, WO 2004/017942.

What is claimed is:

1. Solid amorphous particles comprising an intimate admixture of amorphous tiotropium bromide together with a pharmaceutically acceptable amorphous co-solid selected from dextrose, fructose, glucosamine, glucose, lactose, mannitol, maltitol, mannose, sorbitol, sucrose, trehalose, xylitol or combinations thereof, wherein the term intimate admixture means that substantially all of the individual particles are composed of both the tiotropium bromide and the co-solid.

2. The particles as claimed in claim 1, wherein the co-solid comprises a sugar polyol or an amino sugar.

3. The particles as claimed in claim 1, wherein the co-solid comprises a monosaccharide or a disaccharide.

4. The particles as claimed in claim 1, wherein the co-solid is selected from the group consisting of glucose, lactose, mannitol, mannose, sucrose, trehalose and combinations thereof.

5. The particles as claimed in claim 1, wherein the particles have a particle size of 1-10 microns.

6. The particles as claimed in claim 1, wherein the tiotropium bromide and co-solid are present in a weight ratio of tiotropium bromide to co-solid of from 1:1 to 1:1000.

7. The particles as claimed in claim 6, wherein the weight ratio of tiotropium bromide to co-solid is from 1:10 to 1:500.

8. A process for preparing solid amorphous particles of tiotropium bromide comprising lyophilising an aqueous solution of tiotropium bromide together with a pharmaceutically acceptable co-solid selected from the group consisting of dextrose, fructose, glucosamine, glucose, lactose, mannitol, maltitol, mannose, sorbitol, sucrose, trehalose, xylitol and combinations thereof.

9. The particles as claimed in claim 8, wherein the co-solid comprises a sugar polyol or an amino sugar.

10. The process as claimed in claim 8, wherein the co-solid comprises a monosaccharide or a disaccharide.

11. The process as claimed in claim 8, wherein the co-solid is selected from the group consisting of glucose, lactose, mannitol, mannose, sucrose, trehalose and combinations thereof.

12. A process as claimed in claim 8, further comprising micronising the particles.

13. A process as claimed in claim 8, wherein the particles formed have a particle size of 1-10 microns.

14. Particles as claimed in claim 1, wherein the particles are obtained by a process comprising lyophilising an aqueous solution of tiotropium bromide together with the pharmaceutically acceptable co-solid and wherein the particles are suitable for inhalation.

15. An inhalable medicament comprising the particles as claimed in claim 1 and one or more pharmaceutically acceptable excipients.

16. An inhalable medicament as claimed in claim 15, wherein the medicament is a dry powder and the one or more pharmaceutically acceptable excipients includes an inert carrier.

17. An inhalable medicament as claimed in claim 16, wherein the inert carrier is selected from the group consisting of lactose, glucose, sodium starch glycolate and mixtures thereof.

18. An inhalable medicament as claimed in claim 15, wherein the medicament is an aerosol formulation and the one or more pharmaceutically acceptable excipients includes a propellant.

19. A capsule containing the inhalable medicament as claimed in claim 15.

20. A dry-powder inhaler comprising a chassis, a dosing chamber, a mouthpiece and a medicament as claimed in claim 15.

21. A pressurised metered-dose inhaler comprising a chassis, a mouthpiece and a canister comprising the medicament as claimed in claim 18.

* * * * *